United States Patent [19]

Renner

[11] Patent Number: 4,604,437
[45] Date of Patent: Aug. 5, 1986

[54] POLYMER FROM SUBSTITUTED, UNSATURATED, BICYCLIC IMIDE

[75] Inventor: Alfred Renner, Muntelier, Switzerland

[73] Assignee: Ciba-Geigy Corporation, Ardsley, N.Y.

[21] Appl. No.: 693,640

[22] Filed: Jan. 22, 1985

[30] Foreign Application Priority Data

Jan. 31, 1984 [CH] Switzerland .................. 450/84
Oct. 5, 1984 [CH] Switzerland ................. 4796/84

[51] Int. Cl.$^4$ ............................ C08F 122/40
[52] U.S. Cl. ........................ 526/262; 526/280; 528/322; 548/435
[58] Field of Search .............. 526/262, 280; 528/322

[56] References Cited

U.S. PATENT DOCUMENTS

| | | | |
|---|---|---|---|
| 3,105,839 | 10/1963 | Renner | 260/346.3 |
| 3,334,075 | 8/1967 | Kehn | 260/85.3 |
| 3,450,711 | 6/1969 | Megna et al. | 260/326 |
| 3,839,358 | 10/1974 | Bargain | 260/326.26 |
| 4,229,351 | 10/1980 | Kiefer et al. | 260/326.26 |
| 4,271,074 | 6/1981 | Lohmann et al. | 260/326.26 |
| 4,515,962 | 5/1985 | Renner | 548/435 |

FOREIGN PATENT DOCUMENTS

1277790 6/1972 United Kingdom .

OTHER PUBLICATIONS

A. K. St. Clair et al, Polym. Eng. Sci., 22, 9 (1982).

Primary Examiner—Harold D. Anderson
Attorney, Agent, or Firm—Luther A. R. Hall

[57] ABSTRACT

Imides of the formula I

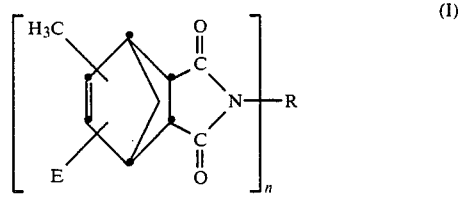

in which E is allyl or methallyl, R is hydrogen, alkyl, alkenyl, cycloalkyl, aryl, benzyl, alkylene or arylene, and n is 1 or 2, are intermediates for the preparation of crosslinked polymers having excellent physical properties. The polymers can be used, in particular, for the preparation of glass fibre-reinforced and carbon fibre-reinforced plastics and heat-resistant composite materials, and as electrical insulation materials and whirl-sintered powder paints.

15 Claims, No Drawings

POLYMER FROM SUBSTITUTED, UNSATURATED, BICYCLIC IMIDE

The invention relates to allyl-substituted or methallyl-substituted methylbicyclo[2.2.1]hept-5-ene-2,3-dicarboximides, to their preparation and to the polymers which can be obtained therefrom by heating.

Maleimides and bismaleimides and also N-allyl-monomaleimides are known.

The curing of halogenated, olefinic rubber polymers by means of selected polymaleimide compounds, such as N,N'-m-phenylene-bismaleimide, is described in U.S. Pat. No. 3,334,075. These polymaleimides do not contain any allyl or norbornenyl groups, and the maleimide radicals do not carry any substituents.

Resin-forming compositions containing maleimide or bismaleimide derivatives, such as N-phenylmaleimide and methylene-bis-(N-phenylmaleimide), are known from British Pat. No. 1,277,790. None of these compounds contains norbornenyl or allyl groups.

A process for the preparation of bismaleimides by reacting a bismaleamic acid with the anhydride of a lower carboxylic acid in the presence of a tertiary amine, an organic solvent and a nickel catalyst is described in U.S. Pat. No. 3,839,358. A process for the preparation of monomaleimides and bismaleimides containing aliphatic substituents on the nitrogen atom is known from U.S. Pat. No. 4,229,351. The preparation of compounds containing allyl-substituted and methyl-substituted norbornenyl groups is not described or suggested either in the former or in the latter patent.

U.S. Pat. No. 3,450,711 relates to bisimide compounds prepared by reacting endo-cis-bicyclo[2.2.1-]hept-5-ene-2,3-dicarboxylic anhydride (=5-norbornene-2,3-dicarboxylic anhydride) with selected organic diamines. These bisimides do not contain either methyl or allyl substituents in the imide radical and are distinguished from the present compounds both by their structure and by their chemical reactivity. The compounds according to this U.S. patent are used as intermediates in the preparation of epoxide compounds.

It is also known that it is possible to prepare polyimide oligomers which are used as adhesives by addition of 3,3',4,4'-benzophenonetetracarboxylic dianhydride onto diaminodiphenylmethane in the presence of various compounds capable of causing crosslinking and end group masking, such as chlorinated or unchlorinated 5-norbornenecarboxylic anhydride and 5-vinylphthalic anhydride [cf., for example, Polym. Eng. Sci., 22, 9–14 (1982)]. These polyimide oligomers do not contain any allyl groups.

Silanes prepared from imide intermediates including, for example, N-allyl-2,3-dimethylmaleimide, are described in U.S. Pat. No. 4,271,074. The monomers according to the invention do not contain any norbornenyl group which is substituted by an allyl group and a methyl group, and are therefore entirely different in structure and are not suggested by this patent.

The preparation of the starting materials for the compounds according to the invention is described in U.S. Pat. No. 3,105,839.

The allyl-substituted or methallyl-substituted methylbicyclo[2.2.1]hept-5-ene-2,3-dicarboximides according to the invention are valuable starting materials for polymers which have excellent properties. They are characterised by formula I below:

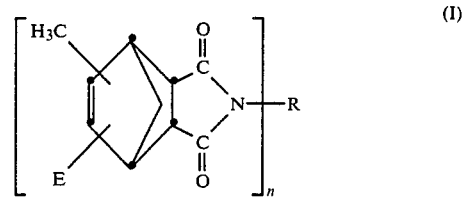

in which E is allyl or methallyl and n is 1 or 2 and, if n is 1, R is hydrogen, alkyl having 1–12 C atoms, alkenyl having 3–6 C atoms, cycloalkyl having 5–8 C atoms, aryl having 6–10 C atoms or benzyl, or, if n is 2, R is —$C_mH_{2m}$— in which m is 2–20, arylene having 6–10 C atoms or a group of the formula II

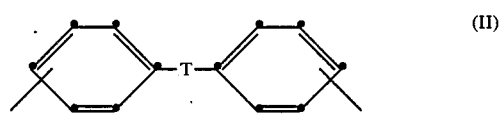

in which

T is methylene, isopropylidene, CO, O, S or $SO_2$.

E is preferably the allyl group.

R can be a linear or branched-chain alkyl group having 1–12 C atoms, such as methyl, ethyl, isopropyl, n-butyl, isopentyl, n-hexyl, 2-ethylhexyl, n-decyl and n-dodecyl, preferably alkyl having 1–8 C atoms.

R can also be a linear or branched-chain alkenyl group having 3–6 C atoms, such as allyl, methallyl, 2-butenyl and 3-hexenyl, preferably allyl.

As a cycloalkyl group, R can be a cyclopentyl, cyclohexyl, cycloheptyl or cyclooctyl group, preferably cyclohexyl.

As an aryl group, R can be unsubstituted phenyl or a phenyl group which is substituted by one or two methyl groups, such as tolyl or xylyl, or naphthyl too. The phenyl group is preferred. As a group —$C_mH_{2m}$—, R can be a linear or branched radical, such as ethylene, propylene, trimethylene, tetramethylene, hexamethylene, octamethylene and dodecamethylene. As a group of the formula II, R is preferably attached to the N atoms in the 4,4'-position.

R is preferably a group —$(CH_2)_m$— in which m is 2 to 12.

As an arylene group having 6–10 C atoms, R can be, for example, an m-phenylene, p-phenylene, 1,3-naphthylene, 1,4-naphthylene, 1,5-naphthylene or 2,6-naphthylene group.

If R is a group of the formula II, T is preferably the methylene group, O or $SO_2$.

Preferred compounds of the formula I are those in which, if n is 1, R is hydrogen, alkyl having 1–8 C atoms, cyclohexyl, allyl or phenyl, or, if n is 2, R is —$(CH_2)_6$— or a group of the formula II in which T is the methylene group or $SO_2$.

Compounds of the formula I which are particularly preferred are those in which n is the number 2 and R is —$(CH_2)_6$—,

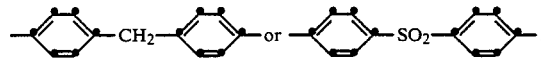

Compounds of the formula I which are very particularly preferred are those in which E is the allyl group and, if n is 1, R is allyl, or, if n is 2, R is —(CH₂)₆— or

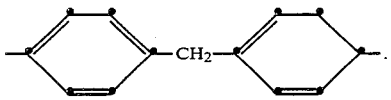

The imides according to the invention can be prepared in a manner known per se, for example by reacting an anhydride of the formula III

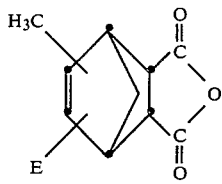     (III)

with a compound of the formula IV (H₂N)ₙR     (IV)

in which E, R and n are as defined under formula I, at an elevated temperature and with removal by distillation of the water formed in the reaction. If the compounds of the formula IV are ammonia or low-boiling monoamines, an excess of these reactants is advisable. It is advantageous to employ diamines in a stoichiometric ratio. The reaction can be carried out without a solvent or in the presence of an inert solvent which can be used for the azeotropic removal of the water (entraining agent). The temperature of the reaction can be between 100° to 250° C. The imides of the formula I are preferably prrepared in the melt under a pressure of not more than 4,500 Pa and at temperatures between 130° and 220° C., in particular 180° and 220° C.

As already mentioned, the starting materials of the formula III can be prepared in accordance with the process described in U.S. Patent Specification No. 3,105,839 by reacting sodium methylcyclopentadienide with an allyl or methallyl halide, followed by a Diels-Alder reaction with maleic anhydride. Although it is stated in the U.S. Patent Specification that the allyl group is attached in the 7-position of the bicyclic system, recent investigations show that an isomeric mixture is formed in respect of the position of the allyl group (in the 1-position and the 6-position) and also in respect of the endo-configuration and exo-configuration of the anhydride moiety. Hitherto it has only been possible to isolate the isomeric components by preparative gas chromatography.

The monoamines or diamines of the formula IV which are used as known or can be prepared by processes known per se.

The compounds according to the invention are liquid, or low-melting solid substances which can be polymerised to give solid products having high glass transition points and good resistance to heat and water. These products can be used for many purposes, for example as casting resins or adhesives and, in particular, for the preparation of glass fibre-reinforced or carbon fibre-reinforced plastics and heat-resistant composite materials, and as electrical insulating materials and whirl-sintered powder paints.

The compounds according to the invention can be used and polymerised without further treatment, or they can first be dissolved in an organic solvent, such as toluene, xylene, methyl ethyl ketone, ethylene glycol monoalkyl and dialkyl ethers having 1-4 C atoms in the alkyl groups or a similar solvent, customary in the paint industry. Solutions of this type can be used as impregnating agents or coating agents or as a form of dispatch to the consumer.

The compounds, according to the invention, of the formula I can be reacted to give novel polymers, and, surprisingly, the methyl substituent hardly impairs the capacity of the allylnorbornene system for polymerisation. Accordingly, the invention also relates to the novel polymers which can be obtained by heating an imide of the formula I at a temperature between 180° and 300° C., preferably between 200° and 250° C., for 6 to 60 hours. In this respect, what has been stated above applies in respect of the preferred meanings of E, R and n. Polymers which are particularly preferred are those which can be obtained by heating an imide of the formula I in which n is the number 2 and R is the group —(CH₂)₆—,

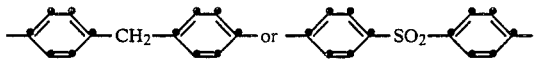

at 240° to 250° C. for 6-24 hours.

It is, of course, possible to add inert and stable substances, such as fillers, pigments, dyes and other additives, to the imides of the formula I before they are polymerised to give crosslinked structures.

PREPARATION EXAMPLES

EXAMPLE 1

Allylmethylbicyclo[2.2.1]hept-5-ene-2,3-dicarboximide

A mixture of 30 g of allylmethylbicyclo[2.2.1]-hept-5-ene-2,3-dicarboxylic anhydride, prepared in accordance with Example 2 of U.S. Pat. No. 3,105,839, and 10.2 g of 25% aqueous ammonia solution is heated at 100°–108° C. for 2.5 hours, with stirring and reflux cooling. According to a gas chromatogram, this gives a mixture of 12 isomers having varying positions for the allyl group and the methyl group in the 1-, 4-, 5- and 6-positions in the bicycloheptene ring, and also exo-anhydrides and endo-anhydrides. Since this mixture of isomers cannot be separated by fractional distillation, it is used for further purposes as such. Water is then removed by distillation, excess ammonia is expelled and the imide is rectified at 140°–145° C. and 2.0 Pa.

21.5 g of a mixture of isomers of allylmethylbicyclo[2.2.1]hept-5-enedicarboxylic acid 2,3-imide are obtained, corresponding to a yield of 71.3% of theory. The imide is a yellow syrup and has a viscosity of 96.18 mPa.s at 80° C.

| Analysis | % C | % H | % N |
|---|---|---|---|
| calculated for C₁₃H₁₅NO₂ | 71.87 | 6.96 | 6.45 |
| found | 71.41 | 6.94 | 6.42 |

IR spectrum:
1639.3 cm⁻¹ cyclic double bond
1653.4 cm⁻¹ allyl group 1708.9 cm$^{-1}$ carbonyl group
1778.0 cm$^{-1}$ carbonyl in the cyclic imide
3210.3 cm$^{-1}$ NH vibration Polymerisation for 48 hours at 250° C. gives a solid having a glass transition temperature (GTT) of 125° C. The IR spectrum contains no absorption bands for

double bonds (1639.2 and 1653.4 cm$^{-1}$).

EXAMPLE 2

Allylmethylbicyclo[2.2.1]hept-5-ene-2,3-dicarboxylic acid N-allylimide

A mixture of 30 g of allylmethylbicyclo[2.2.1]hept-5-ene-2,3-dicarboxylic anhydride and 9.41 g of allylamine is heated at reflux temperature for 2 hours, water is removed by distillation, and the product is rectified at 119°–127° C. and 2.66 Pa. This gives 30.24 g (85.5% of theory) of a pale yellow oil having the following characteristic data: $n_D^{20}=1.5202$, $\eta_{25}=0.135$ Pa.s.

| Analysis | % C | % H | % N |
|---|---|---|---|
| calculated for $C_{16}H_{19}NO_2$ | 74.68 | 7.84 | 5.44 |
| found | 74.66 | 7.55 | 5.22 |

Polymerisation for 48 hours at 250° C. gives a solid having a GTT>250° C. and an IR spectrum which shows no

absorption frequencies (1639.2 and 1653.4 cm$^{-1}$).

EXAMPLE 3

Allylmethylbicyclo[2.2.1]hept-5-ene-2,3-dicarboxylic acid N-(2-ethylhexyl)-imide 30 g of anhydride are reacted with 21.3 g of 2-ethylhexylamine as described in Example 2 above. Distillation at 3.3 Pa gives, between 149° and 162° C., 40.74 g of a yellow oil (90% of theory) having a refractive index $n_D^{20}=1.5090$ and a viscosity of 0.306 Pa.s at 25° C.

| Analysis | % C | % H | % N |
|---|---|---|---|
| calculated for $C_{21}H_{31}NO_2$ | 76.55 | 9.48 | 4.52 |
| found | 76.32 | 9.48 | 4.16 |

Polymerisation for 40 hours at 250° C. gives a solid having a GTT of 128° C. The IR bands for double bonds at 1639.2 and 1653.4 cm$^{-1}$ can no longer be detected.

EXAMPLE 4

Allylmethylbicyclo[2.2.1]hept-5-ene-2,3-dicarboxylic acid N-phenylimide 30 g of anhydride are reacted with 15.4 g of aniline as described in Example 2. The anilide is distilled between 161° and 165° C. at 6.65 Pa to give 23.2 g (57.5% of theory) of a viscous liquid having a viscosity of 4.2 Pa.s at 40° C. and a refractive index $n_D^{20}=1.5647$ at 20° C.

| Analysis | % C | % H | % N |
|---|---|---|---|
| calculated for $C_{19}H_{19}NO_2$ | 77.79 | 6.53 | 4.77 |
| found | 77.92 | 6.46 | 4.68 |

Polymerisation for 48 hours at 250° C. gives a solid having a GTT of 132.5° C. and an IR spectrum which has no absorption frequencies (1639.2 and 1653.4 cm$^{-1}$).

EXAMPLE 5

N,N'-Hexamethylene-bis-(allylmethylbicyclo[2.2.1]hept-5-ene-2,3-dicarboximide)

300 g of allylmethylbicyclo[2.2.1]hept-5-ene-2,3-dicarboxylic anhydride are taken and heated to 130° C., and 79.9 g of melted hexamethylene diamine are added dropwise, with stirring. Water is removed by distillation, the temperature is raised to 180° C. and the pressure is reduced to 53 Pa. 180° C. and 53 Pa are maintained for 15 minutes. This gives 345 g (97% of theory) of a brown, viscous resin having a viscosity of 1.356 Pa.s at 80° C.

| Analysis | % C | % H | % N |
|---|---|---|---|
| calculated for $C_{32}H_{40}N_2O_4$ | 74.39 | 7.80 | 5.42 |
| found | 73.82 | 7.74 | 5.47 |

EXAMPLE 6

Bis-[4-(allylmethylbicyclo[2.2.1]hept-5-ene-2,3-dicarboximidophenyl)]-methane

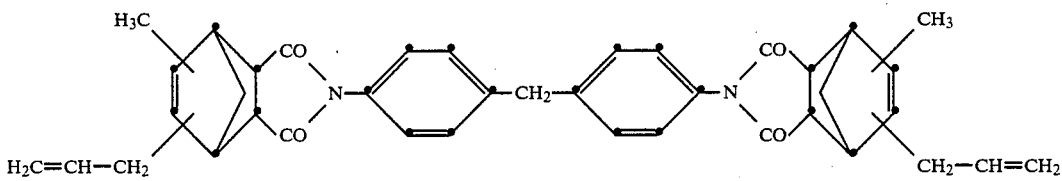

300 g of anhydride and 136.2 g of 4,4'-diaminodiphenylmethane are reacted as described in Example 5. This gives 403.2 g (98.0% of theory) of a dark brown solid resin having a glass transition temperature of 66° C.

| Analysis: | % C | % H | % N |
|---|---|---|---|
| calculated for $C_{39}H_{38}N_2O_4$: | 78.24 | 6.40 | 4.68 |
| found: | 78.41 | 6.49 | 4.68 |

EXAMPLE 7

Bis-[4-(methallylmethylbicyclo[2.2.1]hept-5-ene-2,3-dicarboximidophenyl)]sulfone

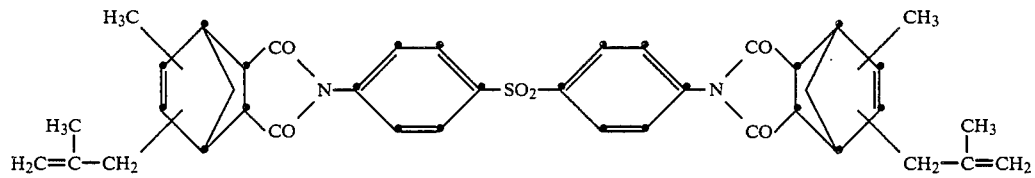

124.15 g of 4,4'-diaminodiphenyl sulfone and 232 g of methallylmethylbicyclo[2.2.1]hept-5-ene-2,3-dicarboxylic anhydride are heated to 180° C., and the pressure is reduced in stages to 25 Pa. After 90 minutes at 180° C. and 25 Pa, 319.55 g of a brown solid resin having a glass transition temperature of 87° C. are obtained.

| Analysis: | % C | % H | % N | % S |
|---|---|---|---|---|
| calculated for $C_{40}H_{40}N_2O_6S$: | 70.98 | 5.96 | 4.14 | 4.74 |
| found: | 69.98 | 5.91 | 4.35 | 4.98 |

The anhydride is prepared analogously to Examples 1 and 2 of U.S. Pat. No. 3,105,839. 994 g of methallyl chloride are used instead of 840 g of allyl chloride. The anhydride, which has not hitherto been described in the literature, distills at 125°–140° C. and 25 Pa, and has $n_D^{20} = 1.508$ and a viscosity of 195 mPa.s.

EXAMPLE 8

Bis-[4-(methallylmethylbicyclo[2.2.1]hept-5-ene-2,3-dicarboximidophenyl)]-methane

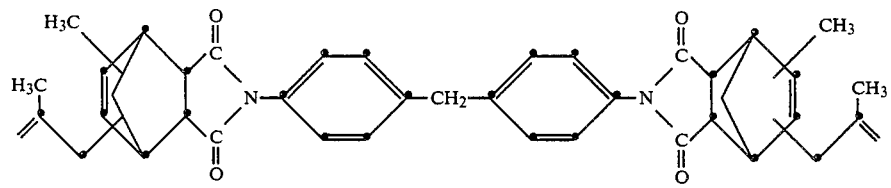

116 g of methallylmethylbicyclo[2.2.1]hept-5-ene-2,3-dicarboxylic anhydride and 49.5 g of 4,4'-diaminodiphenylmethane are heated to 200° C., with stirring, in an atmosphere of $N_2$. 9 cm³ of water are distilled off. In the course of 35 minutes at 200° C. the glass transition temperature rises from 67.5° to 78.5° C. Yield 155 g (99% of theory).

| Analysis: | % C | % H | % N |
|---|---|---|---|
| calculated for $C_{41}H_{42}N_2O_4$: | 78.57 | 6.75 | 4.47 |
| found: | 77.41 | 6.71 | 4.39 |

EXAMPLE 9

Allylmethylbicyclo[2.2.1]hept-5-ene-2,3-dicarboxylic acid N-cyclohexylimide.

A mixture of 20 g of allylmethylbicyclo[2.2.1]hept-5-ene-2,3-dicarboxylic anhydride and 9.09 g of cyclohexylamine is heated at 135° C. for 3 hours, and the product is then distilled in vacuo. 16 g of a yellow, viscous oil distill over between 128° and 138° C. at 2.5 Pa, corresponding to a yield of 58.2%.

| Analysis: | % C | % H | % N |
|---|---|---|---|
| calculated for $C_{19}H_{25}NO_2$: | 76.25 | 8.36 | 4.68 |
| found: | 76.46 | 8.52 | 4.38 |

Thermal polymerisation for 48 hours at 250° C. gives a solid resin having a glass transition temperature of 72.5° C.

The molecule of the compounds according to the invention contains two or more olefinic double bonds which make them capable of polymerisation. Cross-linked polymers having valuable physical properties are obtained on heating, cf. Examples 1–4.

USE EXAMPLES

Example I

The imide prepared in accordance with Example 5 is poured, in the form of a hot, low-viscosity melt, into a steel mould measuring 12×12×0.4 cm and cured for 3 hours at 200°, 3 hours at 225° and 12 hours at 250° C. After cooling, test rods are cut from the sheet. The following properties are measured on these:

| | |
|---|---|
| Flexural strength as specified in DIN 53,452: | 81.5 N/mm² |
| Deflection as specified in DIN 53,452: | 5.2 mm |
| Impact strength as specified in DIN 53,455: | 13.2 kJ/m² |
| Glass transition temperature (TA 2000 made by Mettler) | 201° C. |
| Water absorption (1 hour/100° C.) | 0.48% |
| Tensile shear strength on Anticorodal as specified in DIN 53,283 | 9.9 N/mm² |

Example II

The imide resin prepared in accordance with Example 6 is melted, poured into a steel mould measuring 12×12×0.4 cm and cured for 3 hours at 200°, 3 hours at 225° and 12 hours at 250° C. After cooling, the plate is cut into test rods, on which the following properties are measured:

| | |
|---|---|
| Flexural strength as specified in DIN 53,452: | 95 N/mm² |
| Deflection as specified in DIN 53,452: | 4.5 mm |
| Impact strength as specified in DIN 53,455: | 9.5 kJ/m² |
| Glass transition temperature (TA 2000 made by Mettler) | 192° C. |
| Water absorption (1 hour/100° C.): | 0.35% |
| Tensile shear strength on Anticorodal as specified in DIN 53,283: | 7.6 N/mm² |

The following properties were measured on a test sheet (12×12×0.2 cm):

| | |
|---|---|
| Volume resistivity (DIN 53,482) | $5.0 \times 10^{16}$ cm |
| Dissipation factor (DIN 53,483) | 0.25% |
| Dielectric constant (DIN 53,483) | 3.2 |

Example III

After curing for 24 hours at 250° C., the resin prepared in accordance with Example 7 has a glass transition temperature >250° C. and a tensile shear strength on Anticorodal as specified in DIN No. 53,283 of 9.5 N/mm².

What is claimed is:

1. A polymer obtained by heating an imide of formula I $$\left[ \begin{array}{c} H_3C \\ \\ E \end{array} \bigcirc \begin{array}{c} O \\ \parallel \\ C \\ \\ C \\ \parallel \\ O \end{array} N-R \right]_n \quad (I)$$

in which E is allyl or methallyl and n is 1 or 2 and, when n is 1, R is hydrogen, alkyl having 1-12 C atoms, alkenyl having 3-6 C atoms, cycloalkyl having 5-8 C atoms, aryl having 6-10 C atoms or benzyl, or when n is 2, R is —$C_mH_{2m}$— in which m is 2-20, arylene having 6-10 C atoms or a group of the formula II

[structure II]

in which T is methylene, isopropylidene, CO, O, S or SO₂, at a temperature between 180° and 300° C. for 6 to 60 hours.

2. A polymer according to claim 1 obtained by heating an imide of formula I wherein E is allyl.

3. A polymer according to claim 1 obtained by heating an imide of formula I in which, when n is 1, R is hydrogen, alkyl having 1-8 C atoms, cyclohexyl, allyl or phenyl, or, when n is 2, R is —(CH₂)₆— or a group of the formula II

[structure II]

in which T is the methylene group or SO₂.

4. A polymer according to claim 1 obtained by heating an imide of formula I in which n is the number 2 and R is —(CH₂)₆—,

[structures: —⟨⟩—CH₂—⟨⟩— or —⟨⟩—SO₂—⟨⟩—].

5. A polymer according to claim 1 obtained by heating an imide of formula I in which E is the allyl group and, when n is 1, R is allyl or, when n is 2, R is —(CH₂)₆— or

[structure: —⟨⟩—CH₂—⟨⟩—].

6. A polymer according to claim 1 obtained by heating an imide of formula I in which E is allyl, n is 1 and R is hydrogen.

7. A polymer according to claim 1 obtained by heating an imide of formula I in which E is allyl, n is 1 and R is allyl.

8. A polymer according to claim 1 obtained by heating an imide of formula I in which E is allyl, n is 1 and R is 2-ethylhexyl.

9. A polymer according to claim 1 obtained by heating an imide of formula I in which E is allyl, n is 1 and R is phenyl.

10. A polymer according to claim 1 obtained by heating an imide of formula I in which E is allyl, n is 2 and R is —(CH₂)₆—.

11. A polymer according to claim 1 obtained by heating an imide of formula I in which E is allyl, n is 2 and R is

[structure: —⟨⟩—CH₂—⟨⟩—].

12. A polymer according to claim 1 obtained by heating an imide of formula I in which E is methallyl, n is 2 and R is

[structure: —⟨⟩—CH₂—⟨⟩—].

13. A polymer according to claim 1 obtained by heating an imide of formula I in which E is methallyl, n is 2 and R is

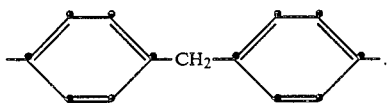
14. A polymer according to claim 1 obtained by heating an imide of formula I in which E is allyl, n is 1 and R is cyclohexyl.
15. A polymer according to claim 1, wherein an imide of the formula I in which n is the number 2 and R is —(CH$_2$)$_6$—,
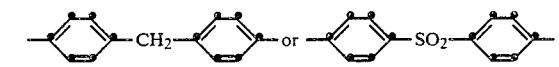
is heated at 200° to 250° C. for 6 to 24 hours.
* * * * *